(12) United States Patent  
Nakamura (10) Patent No.: US 7,018,386 B2
(45) Date of Patent: Mar. 28, 2006

(54) MEDICAL STAND APPARATUS

(75) Inventor: Katsushige Nakamura, Hachioji (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 433 days.

(21) Appl. No.: 10/612,979

(22) Filed: Jul. 7, 2003

(65) Prior Publication Data

US 2004/0097966 A1    May 20, 2004

Related U.S. Application Data

(62) Division of application No. 09/957,070, filed on Sep. 21, 2001, now abandoned.

(30) Foreign Application Priority Data

Sep. 22, 2000  (JP)  .............................. 2000-289074
Sep. 11, 2001  (JP)  .............................. 2001-275721

(51) Int. Cl.
    *A61B 19/00*  (2006.01)
(52) U.S. Cl. ..................... 606/130; 359/384; 248/123.1
(58) Field of Classification Search ................ 606/130, 606/1; 248/127, 132.1, 132.2, 280.11; 600/427, 600/420, 471, 345, 445; 359/384, 368, 382
    See application file for complete search history.

(56) References Cited

U.S. PATENT DOCUMENTS 5,273,039 A    12/1993  Fujiwara et al. ......... 128/653.1
5,397,323 A    3/1995   Taylor et al. ............... 606/130
5,441,505 A    8/1995   Nakamura ................... 606/130
5,528,417 A  * 6/1996   Nakamura ................... 359/384
5,697,939 A    12/1997  Kubota et al. .............. 606/130
5,812,301 A  * 9/1998   Nakamura ................... 359/384
5,818,638 A  * 10/1998  Nakamura ................... 359/384
6,514,239 B1   2/2003   Shimmura et al. ............. 606/1

FOREIGN PATENT DOCUMENTS

EP    0 293 760    12/1988
EP    0 628 290    12/1994
JP    6-197912     7/1994

OTHER PUBLICATIONS

English Language Abstract of JP 6-197912 Copy of European Search Report.

* cited by examiner

*Primary Examiner*—Pedro Philogene
(74) *Attorney, Agent, or Firm*—Michael Bednarek Pillsbury Winthrop Shaw Pittman LLP (57) ABSTRACT

A medical stand apparatus supports light-weight medical equipment and is installable directly on a patient bed or in a small space adjacent to a patient bed.

The medical stand apparatus has a base (10) spaced away from the floor (F), a horizontal rotation member (11), and a protrusion (11*a*). With the use of these elements, the medical stand apparatus directly attaches a parallel link mechanism (6) including a longitudinal sub-link (14) and a lateral sub-link (15) to support the medical equipment to a table (8) on which a patient (7) is laid.

7 Claims, 7 Drawing Sheets

MEDICAL STAND APPARATUS

This application is a division of U.S. patent application Ser. No. 09/957,070, filed Sep. 21, 2001 abandoned.

BACKGROUND OF THE INVENTION

1. Field of the Invention

The present invention relates to a medical stand apparatus.

2. Description of the Related Art

A medical field such as neurosurgery employs a surgical microscope to enlarge and observe a target part and carry out an operation on the target part. The surgical microscope must be easy to use, to shorten an operation time and relieve a patient and an operator of physical and mental fatigue.

The surgical microscope or any other medical equipment is frequently combined with assistant apparatuses for easing the use of the medical equipment. Among the assistant apparatuses, a stand apparatus is used to support the medical equipment. An example of a stand apparatus is disclosed in Japanese Unexamined Patent Publication No. 6-197912. The stand apparatus usually has a parallel link mechanism and a counterweight, to lightly move and stop a heavy surgical microscope at an optional spatial position. With the stand apparatus, an operator may quickly and easily move the surgical microscope like the operator's own limbs to a desired position without assist of actuator, keep the microscope at the position, and orient the microscope toward a target part.

SUMMARY OF THE INVENTION

Conventional stand apparatuses are designed to support large and heavy surgical microscopes and attachments, and therefore, are themselves large and heavy. Accordingly, they are improper to support light medical equipment such as photon radiation systems, endoscopes, or measuring devices. Namely, the conventional stand apparatuses are too bulky to support light medical equipment and are inconvenient to transport and handle.

When a surgical microscope supported by a conventional stand apparatus is moved, a counterweight of the stand apparatus widely shifts its position. The stand apparatus, therefore, needs a large installation space and is unable to install in a narrow space beside a bed, or directly to the bed.

An object of the present invention is to provide a medical stand apparatus that is appropriate to support light medical equipment and is directly installable on a bed or in a narrow space beside a bed.

In order to accomplish the object, a first aspect of the present invention provides a medical stand apparatus 1 having a base 11 fixed to a patient table 8 at a position away from the floor F, a horizontally rotatable member attached to the base and horizontally rotatable around a vertical axis $\alpha 1$ orthogonal to the base, a parallel link mechanism 6 supported by a fulcrum S arranged on the horizontally rotatable member, the link mechanism having a pair of parallel longitudinal links (2,3) and a pair of lateral links (4,5), a support arm 4a extending from the upper lateral link 4 of the link mechanism, to support medical equipment M at a front end thereof, and a counterweight w opposite the medical equipment across the fulcrum, to cancel weight acting in an inclining direction of the link mechanism around the fulcrum S and keep the medical equipment at a spatial position. The front end of the support arm 4a is provided with an end link 12. The link mechanism has a connecting shaft $\beta 1$ serving as a start point of the support arm 4a. To this connecting shaft, a crank 13 is fitted. The crank 13 is connected to a longitudinal sub-link 14 extending in parallel with the longitudinal links and is also connected to a lateral sub-link 15 extending in parallel with the support arm 4a. A lower end of the longitudinal sub-link 14 is articulated at a horizontal protrusion 11a formed on the horizontally rotatable member. An end of the lateral sub-link 15 opposite the crank is articulated at an upper end $\beta 9$ of the end link, so that the end link may always maintain a given posture. A lower end of the end link 12 supports the medical equipment M.

In other words, the first aspect of the present invention provides an assist-less medical stand apparatus 1 for manipulating a medical equipment M used for a patient 7 on a patient table 8 having a first parallel linkage 6 for weight balancing of the apparatus, a second parallel linkage, and a third parallel linkage to cooperatively move with the second parallel linkage for holding the medical equipment and maintaining a posture thereof. The first parallel linkage has a first articulating element $\beta 1$, a second articulating element $\beta 4$, a third articulating element $\beta 3$, and a fourth articulating element $\beta 2$. Where the first articulating element and the second articulating element are linked by a first linkage 2, the second articulating element and the third articulating element are linked by a second linkage 5, the third articulating element and the fourth articulating element are linked by a third linkage 3, the fourth articulating element and the first articulating element are linked by a fourth linkage 4, the third articulating element supports a counterweight, the first linkage 6 is articulated by a fifth articulating element S on a supporting member (10,11), and the supporting member fixes the apparatus with respect to the patient table 8. A second parallel linkage has a sixth articulating element S, a seventh articulating element $\beta 8$, a eighth articulating element $\beta 6$, and a ninth articulating element $\beta 1$. Wherein the sixth articulating element S and the seventh articulating element $\beta 8$ are linked by a sixth linkage 11a, the seventh articulating element $\beta 8$ and the eighth articulating element $\beta 6$ are linked by a seventh linkage 14, the eighth articulating element $\beta 6$ and the ninth articulating element $\beta 1$ are linked by a eighth linkage 13, the ninth articulating element $\beta 1$ and the sixth articulating element S are linked by a fifth linkage 2, the sixth linkage is fixed with respect to the supporting member (10,11), and the fifth linkage and the first linkage are fixed each other. A third parallel linkage has a tenth articulating element $\beta 1$, a eleventh articulating element $\beta 7$, a twelfth articulating element $\beta 9$, and a thirteenth articulating element $\beta 5$. Wherein the tenth articulating element $\beta 1$ and the eleventh articulating element $\beta 7$ are linked by a ninth linkage 13, the eleventh articulating element $\beta 7$ and the twelfth articulating element $\beta 9$ are linked by a tenth linkage 15, the twelfth articulating element $\beta 9$ and the thirteenth articulating element $\beta 5$ are linked by a eleventh linkage 12, the thirteenth articulating element $\beta 5$ and the tenth articulating element $\beta 1$ are linked by a twelfth linkage 4a, the thirteenth articulating element $\beta 5$ are fixed by the fourth linkage 4, the tenth articulating element, the ninth articulating element, and the first articulating element are fixed each other, and the eleventh articulating element $\beta 7$ and the eighth articulating element $\beta 6$ are linked by a thirteenth linkage 13.

A second aspect of the present invention provides a medical stand apparatus 18 having a base (19,20) set on the floor F, a post 21 installed on the base being horizontally articulated about an axis of rotation $\alpha 1$ oriented in a predetermined direction with respect to the base, upper and lower articulations (S1, S2) being provided by the post, a parallel link mechanism 6 supported by the upper articulation S1 and having a pair of parallel longitudinal links (2, 3) and a pair of lateral links (3, 4), a support arm 4a extending from the upper lateral link 4 of the parallel link mechanism, and an end link 12 being supported by a front end of the support arm 4a. The apparatus 18 also has a crank 13 articulated about a first articulation β1 of the parallel link mechanism 6, a longitudinal sub-link 14 parallel with the longitudinal links (2, 3), a lower end of the longitudinal sub-link 14 being articulated by an articulation β8 at a front end of a horizontal first upper protrusion 30 formed on the post, wherein one of the longitudinal links 13 adjacent to the support arm 4a, the crank 13, the longitudinal sub-link 14, and the first upper protrusion 30 form a first auxiliary parallel link. The apparatus 18 further has a lateral sub-link 15 parallel with the support arm 4a, the lateral sub-link 15 cooperatively moving in response to position of the longitudinal sub-link 14 through the crank 13, an upper end of the end link being articulated by an articulation β9 at a first end of the lateral sub-link opposite the crank, wherein the support arm 4a, the upper end of the end link 12, the lateral sub-link 15, and the crank 13 form a second auxiliary parallel link. The apparatus 18 also has an interlocked longitudinal link 22 always parallel with the longitudinal links (2, 3), an upper end of the interlocked longitudinal link being articulated at the lower articulation S2, a lower end of the interlocked longitudinal link being articulated at a first end of an interlocked lateral link β14, a second upper protrusion 2a formed at a lower end of the longitudinal links, a front end of the second upper protrusion being connected to a front end of a lower protrusion 22a formed at an upper end of the interlocked longitudinal link through an interlocked longitudinal sub-link 24, wherein the orientation and length of a straight line between the upper end and lower articulations (β12, β13) of the interlocked longitudinal sub-link 24 are equal to those of a straight line between the upper and lower articulations (S1, S2). Furthermore the apparatus 18 has a weight link 25 connecting an end of the lower lateral link 5 of the parallel link mechanism opposite the medical equipment and a second end of the interlocked lateral link 23, the weight link 25 being parallel with a straight line L2 between the upper articulation S1 and the first end of the interlocked lateral link β14, a counterweight W arranged at the second end of the interlocked lateral link β15, wherein the counterweight cooperatively moves toward and away from the lower articulation S2 in response to movement of the medical equipment M about the upper articulation S1, and the weight of the counterweight acts on the parallel link mechanism 6 to keep the medical equipment at an optional spatial position.

A third aspect of the present invention offsets the lower fulcrum S2 of the second aspect from just below the upper fulcrum S1 toward the medical equipment M side.

A fourth aspect of the present invention provides the end link of any one of the first and second aspects with a first rotation shaft β10 to support a rotary arm 16, and provides the rotary arm with a second rotation shaft β11 orthogonal to the first rotation shaft β10. A holder 17 to hold the medical equipment M is journaled on the second rotation shaft β11. An intersection A of the first and second rotation shafts is set to agree with the gravitational center of the medical equipment M so that the posture of the medical equipment may freely be set. Namely, the rotary arm and holder (16, 17) support the medical equipment so that the medical equipment may freely change its posture. This helps an operator easily and finely adjust the position and posture of the medical equipment.

DESCRIPTION OF THE PREFERRED EMBODIMENT

Embodiments of the present invention will be explained with reference to the accompanying drawings.

Through the drawings, each shaft or articulation is represented with a dot-and-dash center line that corresponds to an axis of rotation thereof.

First Embodiment

FIGS. 1 to 8 show a medical stand apparatus according to the first embodiment of the present invention. The stand apparatus 1 has an articulation S around a principal axis of rotation supporting a parallel link mechanism 6. The link mechanism 6 has a pair of parallel longitudinal links 2 and 3 and a pair of lateral links 4 and 5. The lateral link 4 is extended to form a support arm 4a. A front end of the support arm 4a supports medical equipment M. A counterweight W is provided to cancel weight acting in an inclining direction of the link mechanism 6 around the articulation S and hold the medical equipment M at any spatial position.

The stand apparatus 1 is fitted to a horizontal table 8 on which a patient 7 is laid. The stand apparatus 1 has a base 10 as a support member provided with a fitting unit 9. The fitting unit 9 has a channel-shaped side face and is fitted to an edge of the table 8 away from the floor F. The base 10 has an articulation portion α1 around a principal axis of rotation being substantially orthogonal to the horizontal table 8. A horizontally rotatable member 11 is attached to the base 10. The rotatable member 11 is horizontally articulated about a principal axis of rotation α1. The articulation α1 is provided with an electromagnetic clutch C1 to lock the rotation of the rotatable member 11. On the rotatable member 11, the articulation S of the link mechanism 6 is arranged. A principal axis of the articulation S is substantially orthogonal to that of the articulation α1. The articulation S is provided with an electromagnetic clutch C2 (FIGS. 1 and 3) to lock the rotation of the link mechanism 6 around the articulation S.

Figure 1:
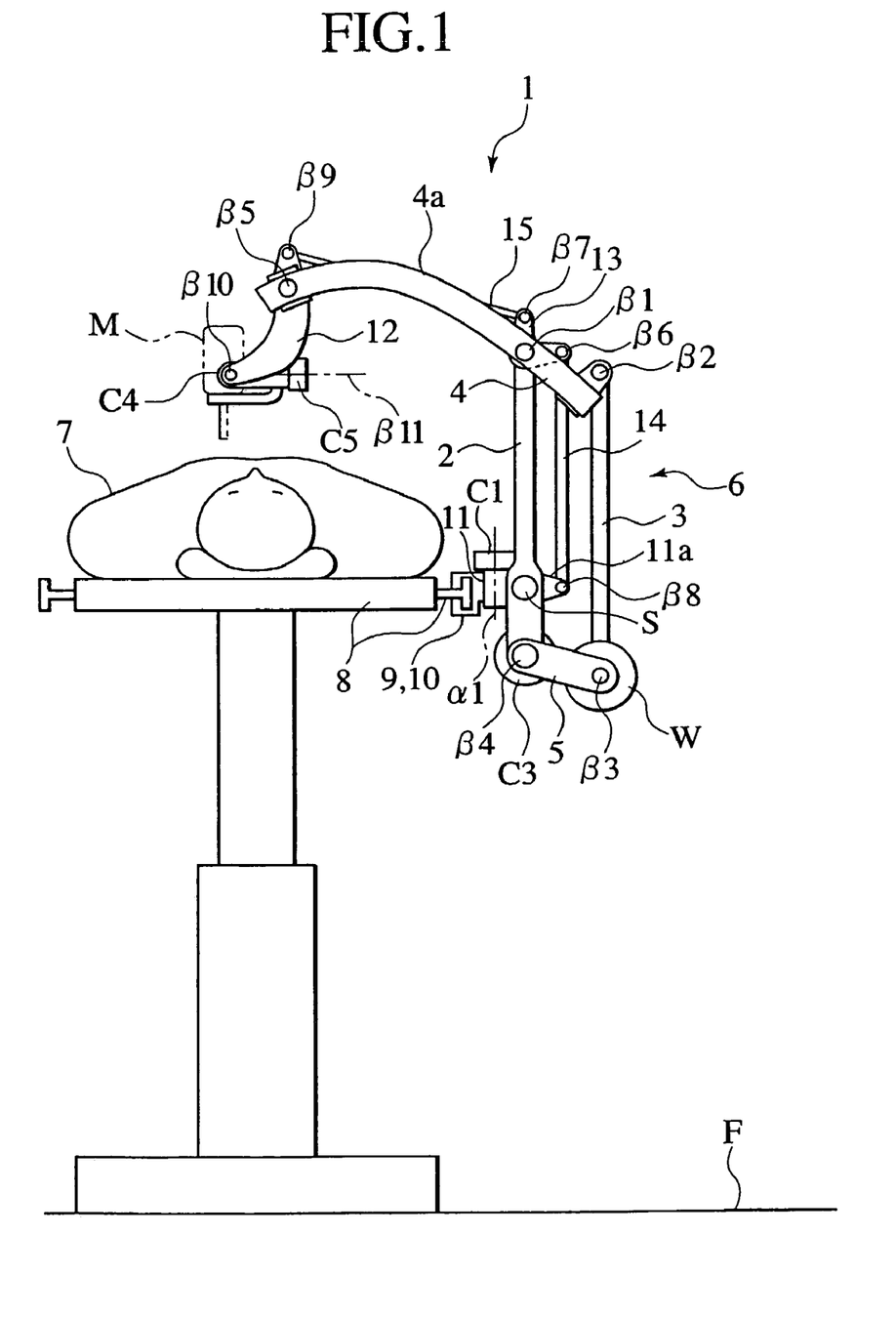
FIG. 1 is a front view showing a medical stand apparatus according to a first embodiment of the present invention.

The parallel link mechanism 6 is formed by connecting the longitudinal links 2 and 3 and the lateral links 4 and 5 to each other at their ends through connecting articulations β1, β2, β3, and β4. In other words, a first parallel linkage for weight balancing of the apparatus 1 is formed by comprising the articulations β1, β2, β3, and β4. The articulation β4 between the links 2 and 5 is provided with an electromagnetic clutch C3 to lock the deformation of the link mechanism 6 in an inclining direction around the articulation β4. The articulation β3 between the links 3 and 5 is provided with the counterweight W. The parallel link mechanism 6 realizes weight balance about the articulation S.

The upper lateral link 4 of the link mechanism 6 is extended to form the support arm 4a. A front end of the support arm 4a has an end link 12 which is rotatable around a connecting articulation β5. The support arm 4a is curved upwardly so that it may not interfere with the head of an operator.

The support arm 4a has a start point on the articulation β1 that supports an L-shaped crank 13. The crank 13 has a horizontal articulation β6 that is on the same horizontal line on which the articulation β1 is present. The crank 13 also has a vertical articulation β7 that is on the same vertical line on which the shaft β1 is present. The articulation β6 is connected to an articulation β8 through a longitudinal sub-link 14. The articulation β8 is arranged at a front end of a horizontal protrusion 11a protruding from the rotatable member 11. The sub-link 14 is parallel with the link 2 and has a length equal to an axial distance between the articulation S and the articulation β1. In other words, a second parallel linkage is formed by comprising the articulations β1, S, β8, and β6. The articulation β7 of the crank 13 is connected to an articulation β9 arranged at an upper end of the end link 12 through a lateral sub-link 15. The sub-link 15 is parallel with a straight line between the articulations β1 and β5 and has a length equal to an axial distance between the articulations β1 and β5. In other words, a third parallel linkage to cooperatively move with the second parallel linkage is formed by comprising the articulations β1, β7, β9, and β5.

As a result, the articulations S, β1, β6, and β8 form an auxiliary parallel link mechanism. And the articulations β1, β5, β9, and β7 form another auxiliary parallel link mechanism. These two parallel link mechanisms of the first and the second parallel linkage are linked by a linkage formed by the crank 13.

Figure 2:
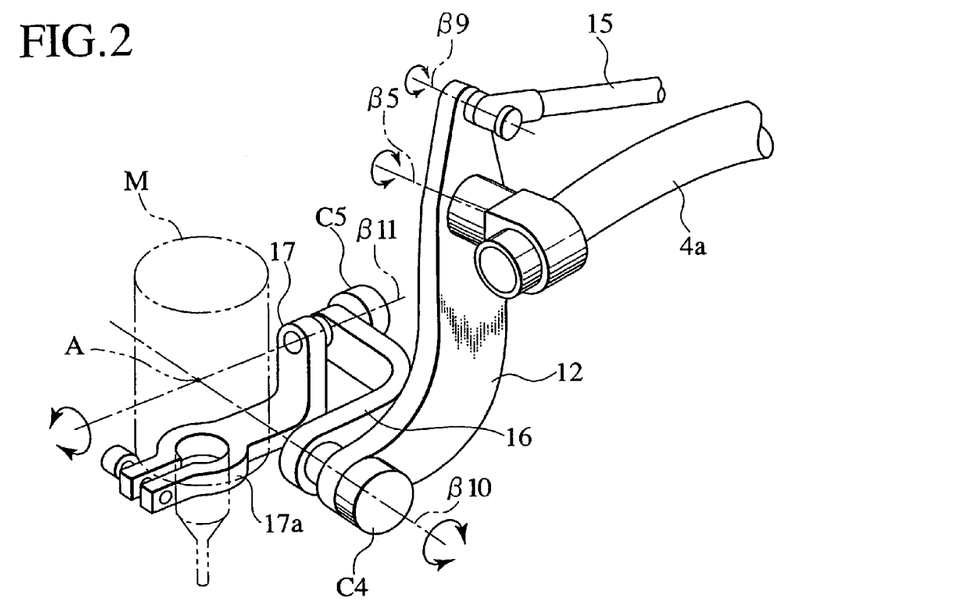
FIG. 2 is a perspective view showing a medical equipment supporting part of the apparatus of FIG. 1.
Figure 3:
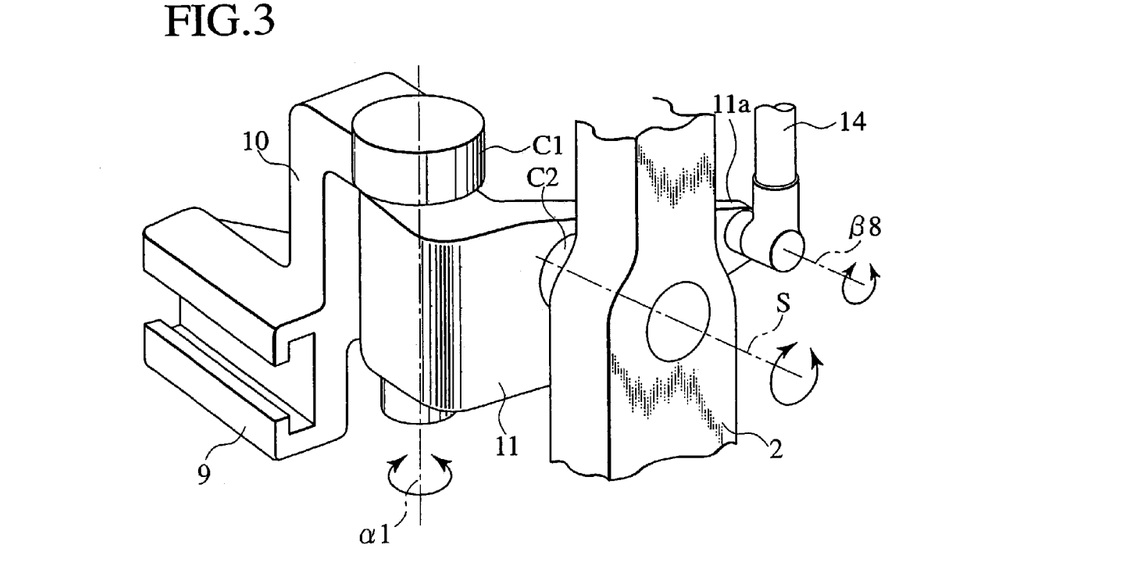
FIG. 3 is a perspective view showing an installation part of the apparatus of FIG. 1.

In FIG. 2, a lower end of the end link 12 has an articulation β10. On the articulation β10, one end of an L-shaped rotary arm 16 is articulated. The rotary arm 16 has another articulation β11 at another end thereof. A principal axis of the articulation β11 is substantially orthogonal to that of the articulation β10. A holder 17 for supporting medical equipment M is articulated by the articulation β11. The holder 17 has a holding part 17a to hold the medical equipment M. Accordingly, the medical equipment M is rotatable in every direction under a held state. The articulations β10 and β11 have electromagnetic clutches C4 and C5, respectively, to lock the rotational position of the medical equipment M. The principal axis of rotation of articulations β10 and β11 are set to have intersection point. Furthermore, the intersection point is set to agree with the gravitational center of the medical equipment M. According to the present invention, the shapes of the rotary arm 16 and holder 17 are optional, provided that the intersection of the articulations β10 and β11 agrees with the gravitational center of the medical equipment M. An angle of the principal axis of the articulation β11 and that of the articulation β10 about the intersection A can be set other than normal.

The stand apparatus 1 according to the embodiment realizes additional weight balance about the principal axis of rotation of the articulation α1. More precisely, opposing parts on each side of the principal axis of rotation α1 show weight balance. The stand apparatus 1 can be symbolized as a mass concentration distribution in a virtual cylindrical space. The cylindrical space has the center axis α1 and can be assumed to comprise plurality of pairs of opposing small spaces with respect to the center axis. If the center axis α1 inclines by an angle θ from a vertical line, a gravity component $\Delta g = g \cdot \sin \theta$ (g being a gravitational acceleration) acts in each small space in a direction orthogonal to the center axis α1. In this case, if the gravitational center of one pair of opposing small spaces is on the center axis α1, no torque about the axis α1 occurs regarding the pair of opposing small spaces. And if the gravitational center of each pair of opposing small spaces is on the center axis α1, weight balance will be established in the cylindrical space around the center axis α1. In this condition, even if the center axis α1 inclines, an object (the stand apparatus) in the virtual cylindrical space causes no rotation around the axis α1.

Even if the table 8 to which the stand apparatus 1 is fixed is inclined, the link mechanism 6 will not spontaneously rotate around the articulation α1 even if the clutch C1 is released. At the same time, the stand apparatus 1 can easily be turned around the articulation α1. Even if the table 8 is inclined, there is no need of carrying out troublesome horizontal adjustment.

Figure 4:
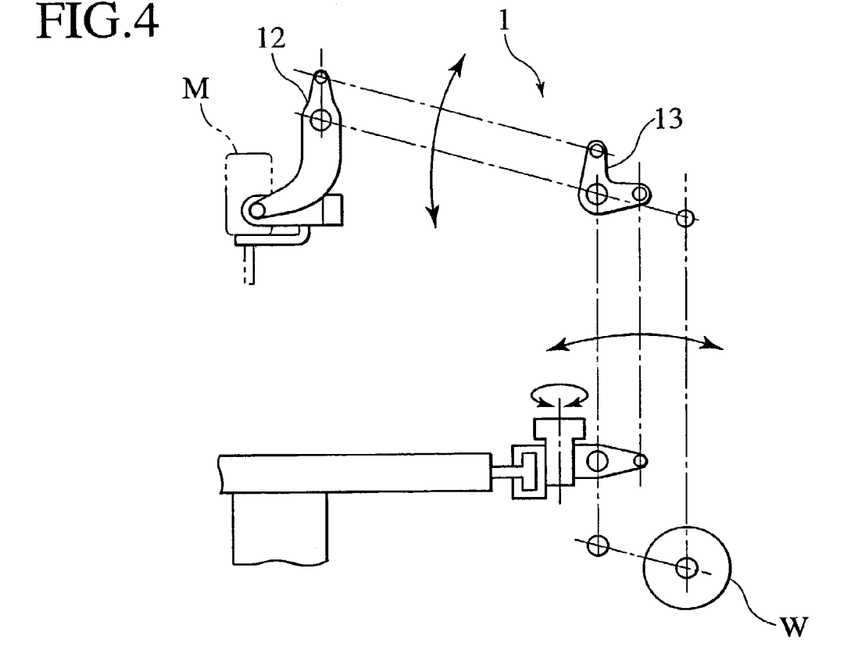
FIG. 4 is a schematic view showing a raised state of a support arm extending from a parallel link mechanism of the apparatus of FIG. 1.
Figure 5:
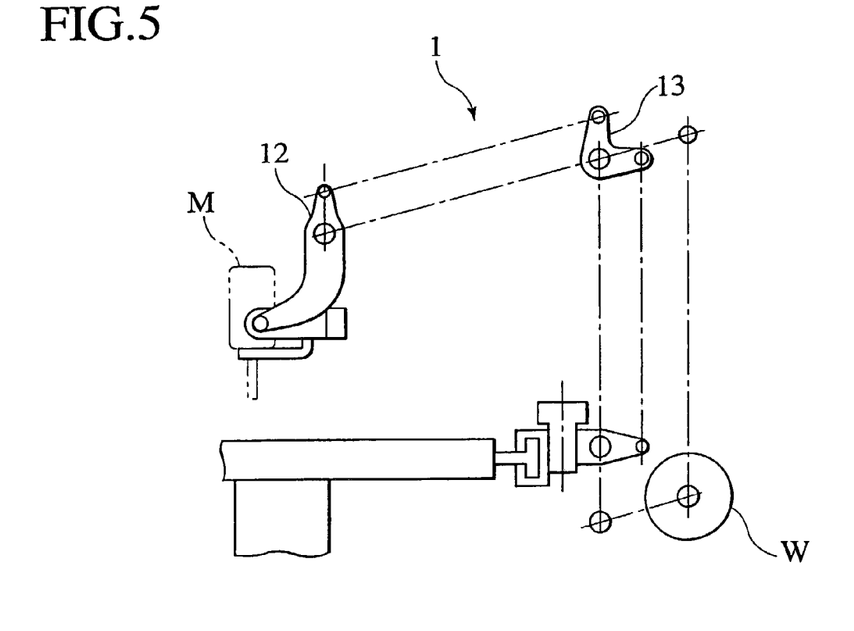
FIG. 5 is a schematic view showing a lowered state of the support arm.
Figure 6:
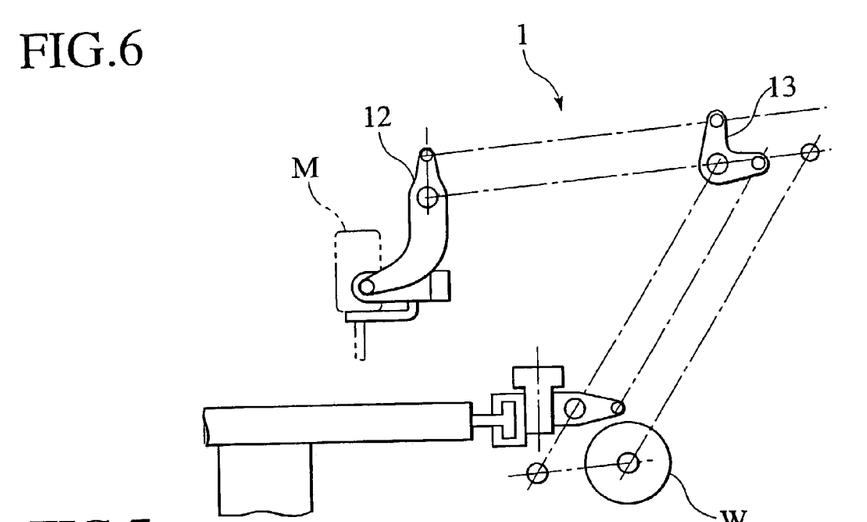
FIG. 6 is a schematic view showing a support arm lowered state with longitudinal links of the link mechanism being inclined to one side.
Figure 7:
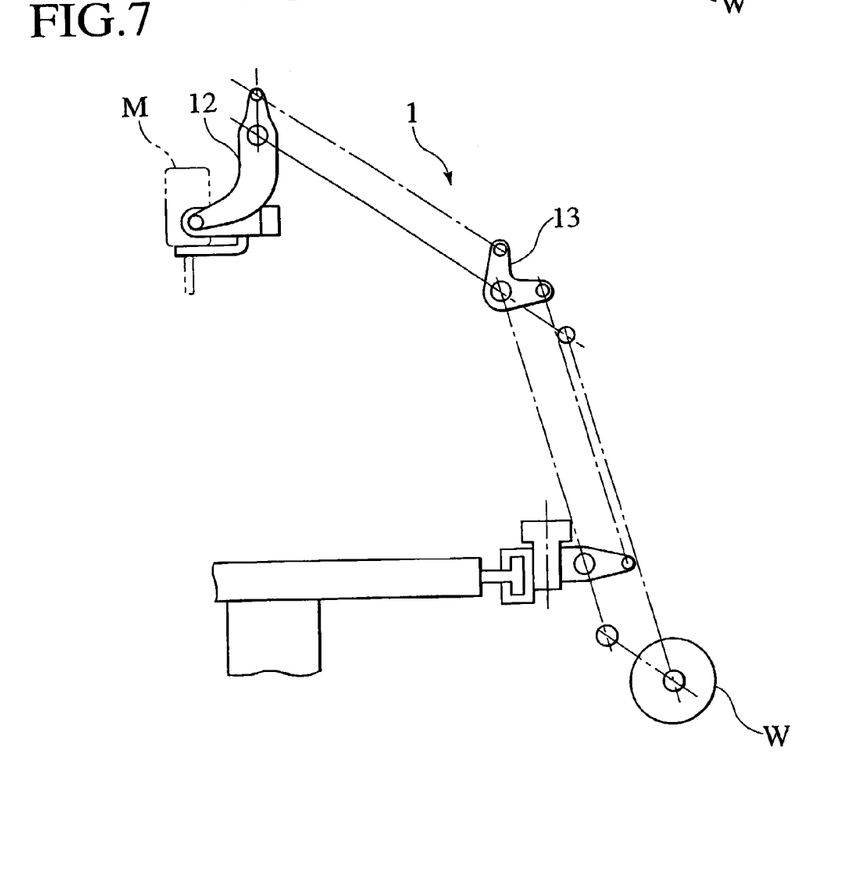
FIG. 7 is a schematic view showing a support arm raised state with the longitudinal links being inclined to the other side.

Mechanical operation of the stand apparatus 1 will be explained with reference to FIGS. 4 to 7. A first characteristic of the stand apparatus 1 is to hold the medical equipment M at an optional spatial position. When the stand apparatus 1 is manipulated to move the medical apparatus M upward and downward (FIGS. 4 and 5), or to and away from the articulation S (FIGS. 6 and 7), the weight of the link mechanism 6, support arm 4a, clutches C1 to C5, medical equipment M, etc., is cancelled by the counterweight W. Therefore the medical equipment M can keep its center of mass at an optional spatial position even if the clutches C2 and C3 are released without assist of any actuator. This will be explained in detail. A vertical change in the posture (position) of the support arm 4a shown in FIGS. 4 and 5 is approximated by fixing the posture (position) of the link mechanism 6, by using the articulation β1 as an imaginary axis of rotation, and by imaginary supporting the counterweight W at the articulation β2. Even if the support arm 4a is vertically moved, weight balance around the imaginary axis β1 is maintained. In FIG. 6, the posture of the support arm 4a shown in FIG. 5 is maintained and the inclination angle of the link mechanism 6 is changed. In this case, the link mechanism 6 maintains weight balance between the medical equipment M, etc., and the counterweight W about the articulation S. By combining the vertical and horizontal posture changes mentioned above, the medical equipment M may be moved to an optional spatial position as shown in FIG. 7 without breaking weight balance. At any position of the medical equipment M, weight balance about the principal axis of rotation of the articulation α1 is also maintained according to the embodiment.

A second characteristic of the stand apparatus 1 is to always maintain a given position/posture of the end link 12 through a combination of the auxiliary parallel link mechanism made of the articulations S, β1, β6, and β8 and the auxiliary parallel link mechanism made of the articulations β1, β5, β9, and β7. These two auxiliary link mechanisms are connected to each other through the crank 13, to always maintain a fixed relationship between the orientation of a straight line between the articulations S and β8 and the orientation of a straight line between the articulations β5 and β9 due to their cooperative linkage. The positions of the articulations S and β8 are fixed on the rotatable member 11 in order to always maintain a fixed posture of the end link 12.

When the support arm 4a is vertically moved around the articulation β1, or when the link mechanism 6 is inclined around the articulation S to horizontally move the medical equipment M with respect to the table 8 as shown in FIGS. 4 to 7, the end link 12 always maintains a given posture. Even if the medical equipment M is horizontally and vertically moved by deforming the link mechanism 6, the end link 12 always maintains a fixed posture. As a result, the holding state of the medical equipment M is unchanged, the end link 12 does not rotate, and the end link 12 does not interfere with the head of an operator while the stand apparatus is being handled.

A third characteristic of the stand apparatus 1 is to cause no spontaneous rotation of the medical equipment M about the articulations β10 and β11. This is realized by intersecting of the articulations β10 and β11 and setting the intersection A at the gravitational center of the medical equipment M. When the clutches C4 and C5 are released, the medical equipment M is freely rotatably in every direction and is kept balanced. As a result, auto regulation of posture of the medical equipment M is achieved by linkage of the auxiliary parallel link mechanisms and by the agreement of the intersection A of the articulations β10 and β11 and the gravitational center of the medical equipment M besides of weight balances about the articulation S and the articulation α1. Therefore assist-less manipulation of stand apparatus for keeping the medical equipment M at optional spatial position or moving it thereto.

With these three characteristics, the stand apparatus 1 is capable of simultaneously changing the position/posture of the medical equipment M by releasing the clutches C1 to C5 and maintaining the changed position or posture. This is like establishing a gravity-free space around the medical equipment M and floating the medical equipment M in the space according to the weight balances. Any optional position/posture of the stand apparatus 1 is a kind of unstable balanced position. Therefore, the medical equipment M supported by the stand apparatus 1 is capable of adjusting its position and posture in response to even a fine motion of an operator or a patient.

An embodiment applicable to an actual medical scene will be explained. FIG. 2 shows a cancer reappearance preventive photon radiation system serving as the medical equipment M. The photon radiation system is supported by the stand apparatus 1 and is weakly linked to a patient, so that a photon radiation position may follow a target part of the patient in response to even a fine motion such as a breathing motion of the patient. As a result, the photon radiation system may effectively work to surely prevent the reappearance of cancer.

Figure 8:
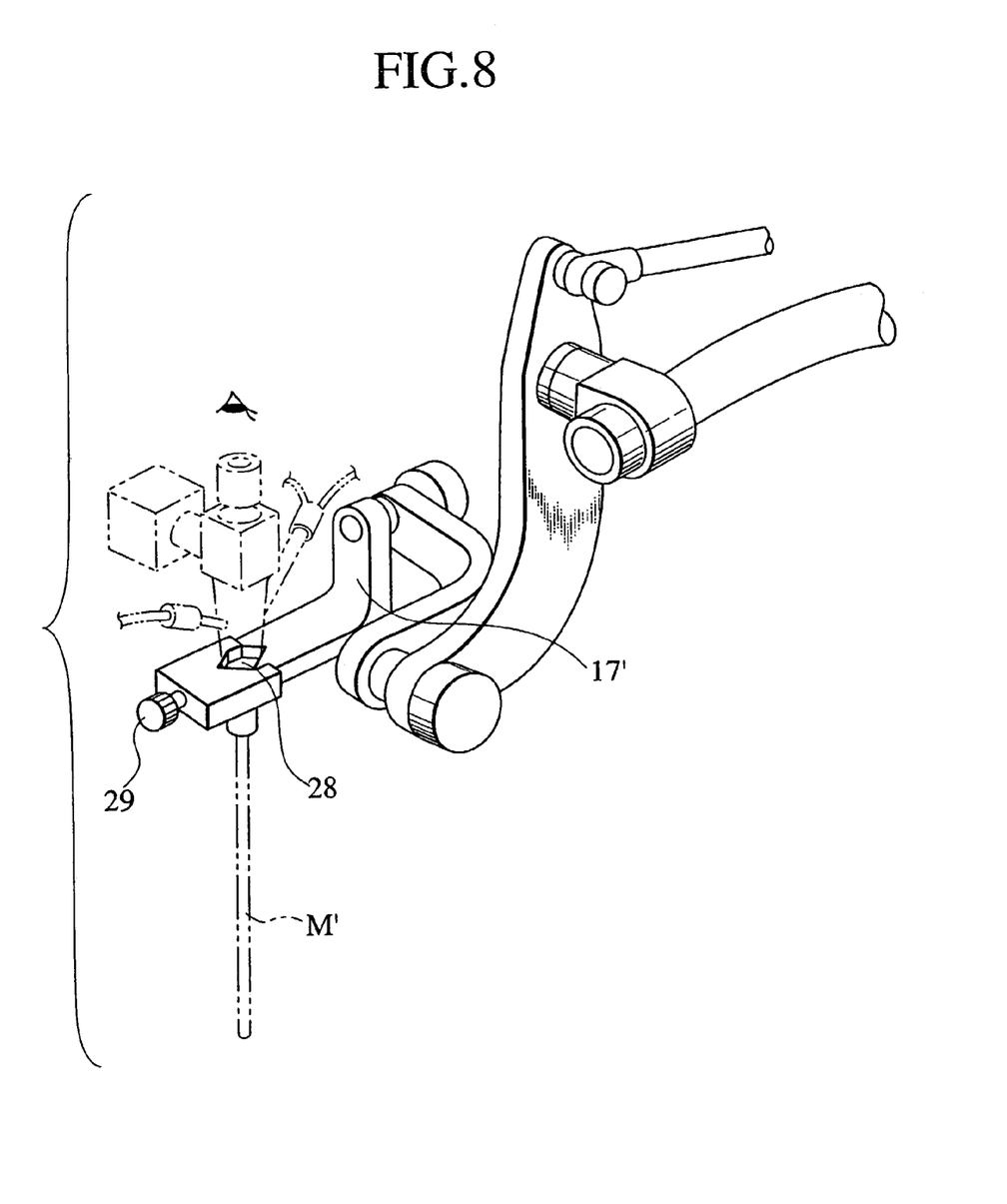
FIG. 8 is a perspective view showing an endoscope supported by the stand apparatus.

FIG. 8 shows an endoscope serving as medical equipment M' supported by the stand apparatus 1. The stand apparatus 1 is provided with a holder 17' having a holding part 28 to hold the medical equipment M'. The holding part 28 has opposing V shapes and a knob 29, which is turned to hold and release the endoscope. According to prior arts, an operator must hold an endoscope, insert a front end of the endoscope into the respiratory tract or esophagus of a patient, and manipulate an actuator to operate a target part. In this case, the operator must hold the endoscope for a long time with one hand and control the front end of the endoscope with the other hand. This puts heavy burden on the operator and requires the operator to have skills. On the contrary, the stand apparatus 1 of the embodiment holds, for the operator, the endoscope and moves like the limbs of the operator. Accordingly, the operator can concentrate on controlling the front end of the endoscope in the respiratory tract or esophagus of the patient and operate a target part with the use of the actuator. In this way, the stand apparatus 1 of the embodiment serves as a powerful helper to relieve a burden from the operator and shorten an operation time.

Second Embodiment

Figure 9:
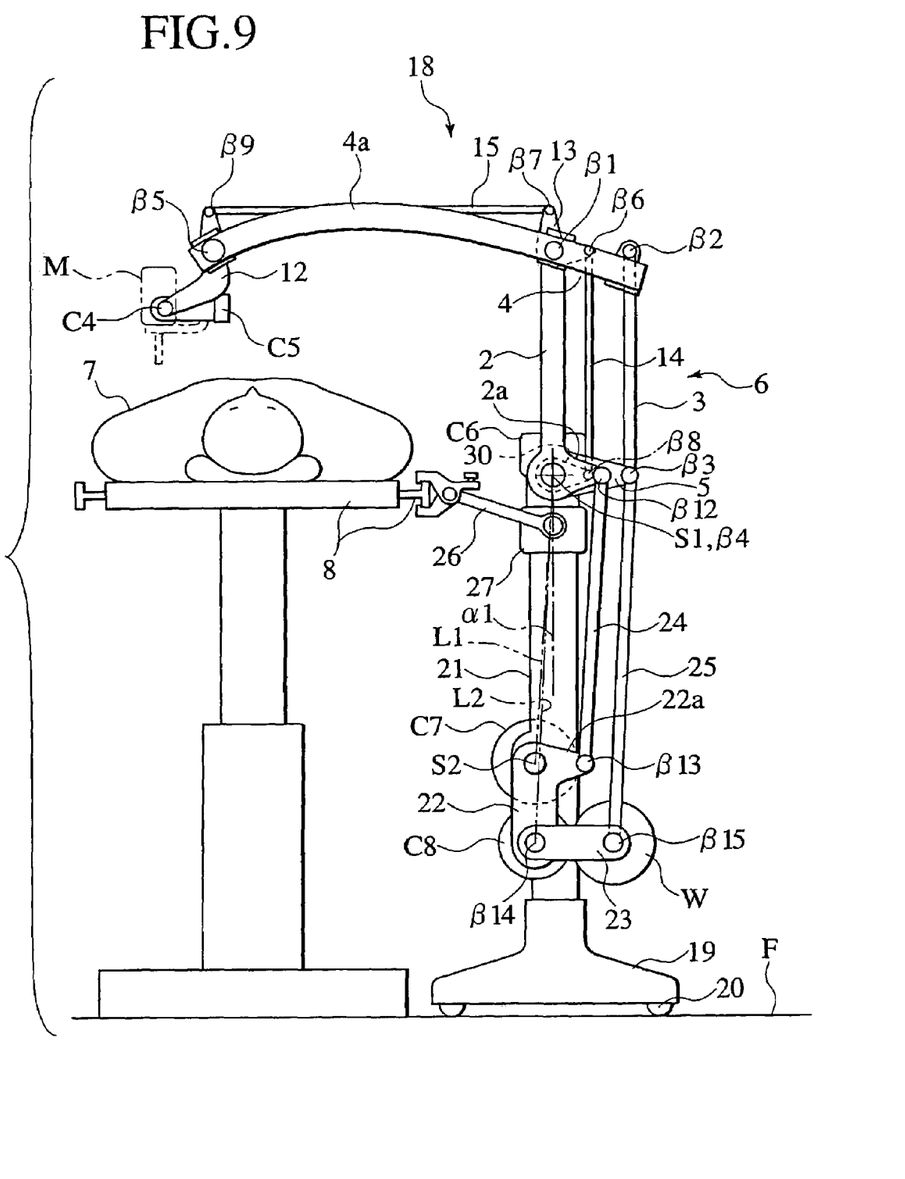
FIG. 9 is a front view showing a medical stand apparatus according to a second embodiment of the present invention in a state that main axes of a link 2 and a post 21 are substantially agree with each other.
Figure 10:
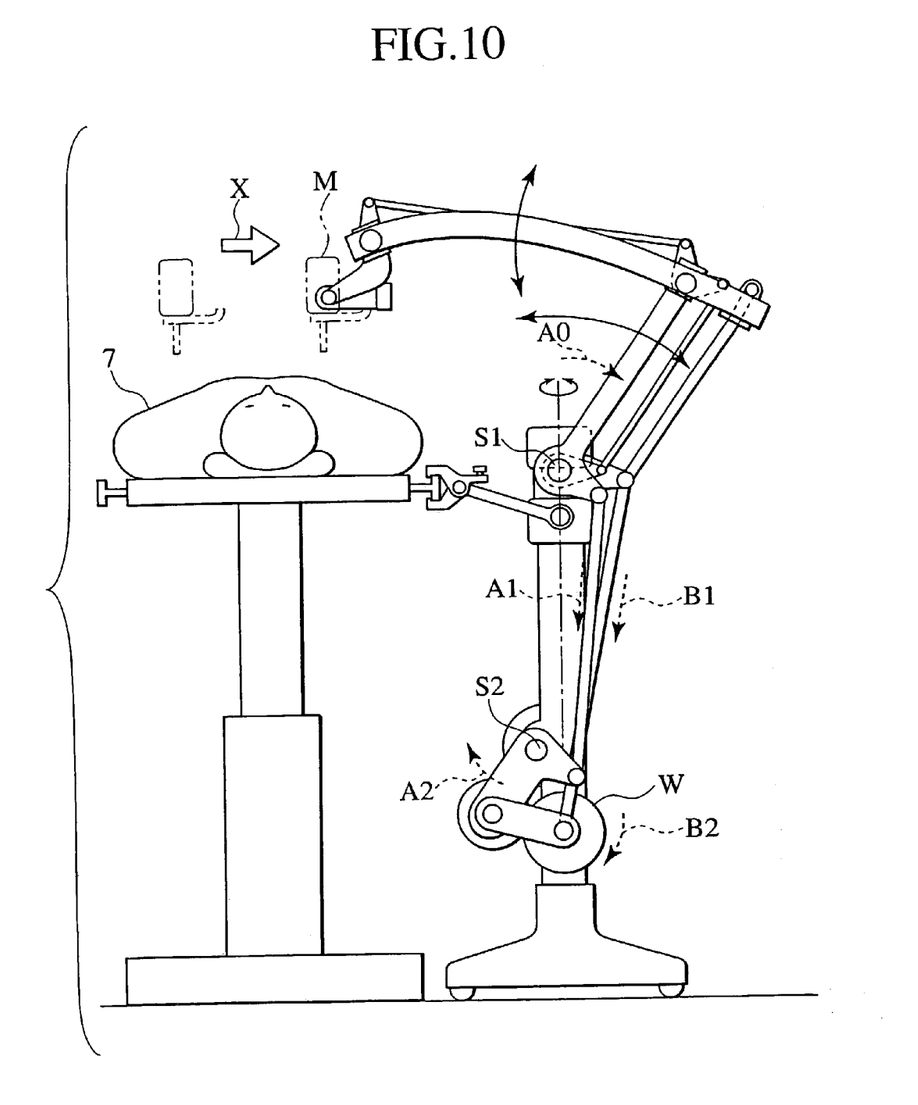
FIG. 10 is a front view showing an inclined state of a parallel link mechanism of the apparatus of FIG. 9.

FIGS. 9 and 10 show a stand apparatus 18 according to the second embodiment of the present invention. A counterweight W of the stand apparatus 18 is close to the floor F. Like parts are represented with like reference numerals in the first and second embodiments and their explanations will not be repeated.

The stand apparatus 18 has a base 19 provided with casters 20 having a locking mechanism (not shown). When the locking mechanism is released, the base 19 with the casters 20 can move on the floor F. The base 19 has a post 21 that is rotatable about a vertical axis of rotation α1. The base 19 and post 21 form a support base. The post 21 is provided with an electromagnetic clutch C6 to lock the rotation of the post 21.

The post 21 has upper and lower articulations S1 and S2. The lower articulation S2 is offset from just below the upper articulation S1 toward the medical equipment M side. A parallel link mechanism 6 is articulated at a principal axis of rotation β4 as the same as that of the upper articulation S1. An upper end of an interlocked longitudinal link 22 is articulated about a principal axis of rotation S2. When the main axes of a link 2 and the post 21 are substantially agree with each other as shown in FIG. 9, the upper articulation S1 is offset from an extension of a straight line between the lower articulation S2 and a connecting articulation β14.

At the upper articulation S1, the post 21 has a first upper protrusion 30. A straight line between the upper articulation S1 and an articulation β8 on the first upper protrusion 30 is equal in length to and parallel with a straight line between a articulation β1 and a horizontal articulation β6 on a horizontal part of a crank 13. The articulation β8 at a front end of the first upper protrusion 30 is connected to the articulation β6 of the crank 13 through a longitudinal sub-link 14 that is parallel with the link 2.

In FIG. 9, a lower end of the link 2 has a horizontally protruding second upper protrusion 2a. An upper end of the link 22 has a lower protrusion 22a that is equal in length to and parallel with the second upper protrusion 2a. Namely, the length and orientation of a straight line between the upper articulation S1 and a articulation β12 on the protrusion 2a are equal to those of a straight line between the lower articulation S2 and a articulation β13 of the link 22. The articulation β12 at the front end of the protrusion 2a is connected to the articulation β13 at the front end of the protrusion 22a through an interlocked longitudinal sub-link 24 that is parallel with a straight line L1 between the upper articulation S1 and the lower articulation S2. The upper articulation S1, articulations β12 and β13, and lower articulation S2 form a first auxiliary parallel link mechanism to always maintain the posture of the link 22 to be parallel with the posture of the link 2.

An articulation β3 of a lower lateral link 5 of the link mechanism 6 opposite the medical equipment M is connected to an articulation β15 of an interlocked lateral link 23 through a weight link 25. The weight link 25 is parallel with a straight line L2 extending between the upper articulation S1 and a articulation β14 at a lower end of the link 22. The articulations β14, β15, β3, and β4 form an imaginary second auxiliary parallel link mechanism to substantially equalize the posture (position) of the link 23 with that of the link 5. Namely, the links 23 and 5 are parallel with each other.

The articulation β15 is provided with the counterweight W that acts on the articulation β3 of the link mechanism 6 through the weight link 25. The lower articulation S2 is provided with an electromagnetic clutch C7, and the articulation β14 of the link 22 with an electromagnetic clutch C8. The clutch C7 locks a motion related to the sub-link 24, and the clutch C8 locks a motion related to the weight link 25.

Mechanical operation of the stand apparatus 18 will be explained. In FIG. 10, the medical equipment M is horizontally moved in an X-direction indicated with an arrow mark. This movement inclines the link 2 and slightly lifts a support arm 4a. If only the link 2 is inclined without raising the support arm 4a, the articulation β1 will go down to lower the medical equipment M. This is not preferable. The first auxiliary parallel link causes interlocked movements of A0, A1, and A2 indicated with dotted arrow marks. As a result, the link 22 inclines with the link 2. Further, the imaginary second auxiliary parallel link causes interlocked movements of B1 and B2 to move the counterweight W toward the lower articulation S2. Namely, if the position of the medical equipment M is changed around the upper articulation S1, the counterweight W is moved to or away from the lower articulation S2 accordingly. The counterweight W acts on the articulation β3 through the weight link 25, thereby canceling weight acting in the inclining direction of the link mechanism 6. Then, like the first embodiment, the stand apparatus 18 of the second embodiment keeps the medical equipment M at an optional spatial position. Substantially no external force is needed to move the medical equipment M according to the second embodiment, and therefore, one can move the medical equipment M as if it is in a gravity-free state.

The second embodiment arranges the counterweight W at a lower position close to the lower articulation S2 for stabilizing the stand apparatus 18. The post 21 has an externally inserted cylinder 27 and an arm 26 attached to the cylinder 27. The arm 26 is fixed to a patient table 8, so that the stand apparatus 18 may support heavier medical equipment.

According to this embodiment, the counterweight W is supported at a location away from the upper articulation S1. In spite of this, the counterweight W will not widely move when the link 2 is inclined. In addition, the position of the articulation β14 is corrected by the link 22 in response to the inclination of the link 2. This results in generating the motion B2 mentioned above, to correct the position of the support arm 4a.

In this way, the movement of the counterweight W is small and occurs in the vicinity of the post 21 due to the offset of the lower articulation S2. Accordingly, the stand apparatus 18 of the second embodiment can be installed in a narrow space. According to the second embodiment, the base 19 is set on the floor. Instead, the stand apparatus of the second embodiment may employ a base (not shown) to be attached to an edge of the patient table 8.

Although the embodiments have been explained in connection with, as examples of light-weight medical equipment, the photon radiation system, endoscope, measuring device, etc., the present invention is not limited to these examples. For example, the present invention may handle, as light-weight medical equipment, a surgical microscope. There are many light-weight surgical microscopes that are small or weigh-reduced by removing accessories such as assistant mirrors and video cameras. These surgical microscopes are supportable by the stand apparatus of the present invention.

As mentioned above, the medical stand apparatus according to the first embodiment employs a base positioned away from the floor, a horizontally rotatable member, and a protrusion, to directly attach, to a patient table, a parallel link mechanism that includes longitudinal and lateral sub-links to support medical equipment. This stand apparatus needs no installation space on the floor and is appropriate to support light-weight medical equipment.

The medical stand apparatus according to the second embodiment employs a base arranged on the floor, a post, a first upper protrusion, a second upper protrusion, a lower protrusion, an interlocked longitudinal sub-link, and a weight link. With these elements, the second embodiment installs, in a narrow space, a parallel link mechanism including longitudinal and lateral sub-links to support medical equipment. The stand apparatus of the second embodiment needs no large space required by conventional stand apparatuses and is appropriate to support light-weight medical equipment.

The present disclosure relates to subject matter contained in Japanese Patent Applications No. 2000-289074, filed on Sep. 22, 2000, and No. 2001-275721, filed on Sep. 11, 2001, the disclosure of which is expressly incorporated herein by reference in its entirety.

What is claimed is:

1. A medical stand apparatus comprising:
   a base set on the floor, the base having a post installed on the base, the post being horizontally articulated about an axis of rotation oriented in a predetermined direction with respect to the base, the post being provided with upper and lower articulations;
   a parallel link mechanism supported by the upper articulation, the parallel link having a pair of parallel longitudinal links and a pair of lateral links;
   a support arm extending from the upper lateral link of the parallel link mechanism, a front end of the support arm supporting an end link;
   a crank articulated about a first articulation of the parallel link mechanism, the first articulation serving as a start point of the support arm;
   a longitudinal sub-link parallel with the longitudinal links, a lower end of the longitudinal sub-link being articulated at a front end of a horizontal first upper protrusion formed on the post, one of the longitudinal links adjacent to the support arm, the crank, the longitudinal sub-link, and the first upper protrusion forming a first auxiliary parallel link;
   a lateral sub-link parallel with the support arm, the lateral sub-link cooperatively moving in response to position of the longitudinal sub-link through the crank, an upper end of the end link being articulated at a first end or the lateral sub-link opposite the crank, the support arm, the upper end of the end link, the lateral sub-link, and the crank forming a second auxiliary parallel link;
   an interlocked longitudinal link always parallel with the longitudinal links, an upper end of the interlocked longitudinal link being articulated at the lower articulation, a lower end of the interlocked longitudinal link being articulated at a first end of an interlocked lateral link;

a second upper protrusion formed at a lower end of the longitudinal links, a front end of the second upper protrusion being connected to a front end of a lower protrusion formed at an upper end of the interlocked longitudinal link through an interlocked longitudinal sub-link, the orientation and length of a straight line between upper and lower articulations of the interlocked longitudinal sub-link being equal to those of a straight line between the upper and lower articulations;

a weight link connecting an end of the lower lateral link of the parallel link mechanism opposite the medical equipment and a second end of the interlocked lateral link, the weight link being parallel with a straight line between the upper articulation and the first end of the interlocked lateral link; and a counterweight arranged at the second end of the interlocked lateral link, the counterweight cooperatively moving toward and away from the lower articulation in response to movement of the medical equipment about the upper articulation, the weight of the counterweight acting on the parallel link mechanism to keep the medical equipment at an optional spatial position.

2. The medical stand apparatus of claim 1, wherein
the lower articulation is offset from just below the upper articulation toward the medical equipment.

3. An assist-less medical stand apparatus for manipulating a medical equipment used for a patient on a patient table comprising:

a first articulation positioned at a first end of a first link;

a second articulation positioned at a second end of the first link, the second articulation being arranged at a predetermined position on a base;

a third articulation positioned at a first end of a second link;

a fourth articulation positioned at a second end of the second link, the first articulation, the third articulation, the fourth articulation, and the second articulation forming a first parallel link mechanism;

a fifth articulation positioned at a first end of a third link at a predetermined position with respect to the base;

a sixth articulation positioned at a second end of the third link, the first articulation, the sixth articulation, the fifth articulation, and the second articulation forming a second parallel link mechanism;

a seventh articulation positioned at a front end of a support arm extending from the first articulation;

an eighth articulation positioned at a first end of a fourth link;

a ninth articulation positioned at a second end of the fourth link, the eighth articulation and the ninth articulation being linked by an end link for holding the medical equipment and keeping a position thereof, the eighth articulation, the ninth articulation, the seventh articulation, and the first articulation forming a third parallel link mechanism;

a tenth articulation positioned below the second articulation on the base;

an eleventh articulation positioned at a first end of a fifth link;

a twelfth articulation positioned at a second end of the fifth link, and the second articulation, the eleventh articulation, the twelfth articulation, and the tenth articulation forming a fourth parallel link mechanism;

a thirteenth articulation positioned at a first end of a sixth link and supporting a counterweight, and a second end of the sixth link being articulated on the fourth articulation; and a fourteenth articulation positioned at a first end of a seventh link, a second end of the seventh link being articulated on the thirteenth articulation, wherein:

the third and second parallel link mechanisms cooperate with each other through a linkage between the sixth and eighth articulations; and the tenth and fourteenth articulations are linked with an eighth link which cooperates with the fourth parallel link mechanism.

4. The apparatus of claim 3, wherein
the tenth articulation is offset from just below the second articulation toward the medical equipment.

5. The apparatus of claim 3 wherein the base is set on the floor.

6. The apparatus of claim 3, further comprising a rotary arm articulated on the end link about a first principal axis of rotation, the rotary arm having a holder articulated on the rotary arm about a second principal axis of rotation, the first principal axis of rotation and the second principal axis of rotation intersecting, and the intersection being set to agree with the gravitational center of the medical equipment.

7. The apparatus of claim 6 wherein the first principal axis of rotation and the second principal axis of rotation are substantially orthogonal to each other.

* * * * *